United States Patent [19]
Bodicky et al.

[11] Patent Number: 4,895,147
[45] Date of Patent: Jan. 23, 1990

[54] LANCET INJECTOR

[75] Inventors: Raymond O. Bodicky, Oakville, Mo.; Ronald W. Ausherman, Bethalto, Ill.

[73] Assignee: Sherwood Medical Company, St. Louis, Mo.

[21] Appl. No.: 264,291

[22] Filed: Oct. 28, 1988

[51] Int. Cl.$^4$ .............................................. A61B 17/32
[52] U.S. Cl. ..................................... 606/182; 128/770
[58] Field of Search .............. 128/314, 760, 763, 765, 128/770; 604/117

[56] References Cited

U.S. PATENT DOCUMENTS

| | | | |
|---|---|---|---|
| 55,620 | 6/1866 | Canewell | 128/314 |
| 59,306 | 10/1866 | Wolff. | |
| 3,030,959 | 4/1962 | Grunert | 128/314 |
| 3,656,472 | 4/1972 | Moura | 128/2 R |
| 3,741,197 | 6/1973 | Sanz et al. | 128/314 |
| 4,203,446 | 5/1980 | Hofert et al. | 128/329 R |
| 4,360,016 | 11/1982 | Sarrine | 128/763 |
| 4,388,925 | 6/1983 | Burns | 128/314 |
| 4,416,279 | 11/1983 | Lindner et al. | 128/314 |
| 4,449,529 | 5/1984 | Burns et al. | 128/314 |
| 4,462,405 | 7/1984 | Ehrlich | 128/314 |
| 4,469,110 | 9/1984 | Slama | 128/770 |
| 4,503,856 | 3/1985 | Cornell et al. | 128/314 |
| 4,627,445 | 12/1986 | Garcia et al. | 128/770 |
| 4,637,403 | 1/1987 | Garcia et al. | 128/770 |
| 4,653,513 | 3/1987 | Dombrowski | 128/765 |

FOREIGN PATENT DOCUMENTS

| | | |
|---|---|---|
| 459483 | 4/1928 | Fed. Rep. of Germany . |
| 567627 | 3/1924 | France . |

*Primary Examiner*—Max Hindenburg
*Attorney, Agent, or Firm*—Andrew J. Beck; Montgomery W. Smith; Richard D. Allison

[57] ABSTRACT

An improved lancet injector is provided which includes an elongate tubular housing, a penetration depth selector thereon, a moveable lancet guide in the housing and a compressible spring in the housing connected between the lancet guide and one end of the housing. The lancet guide further including a flexible plunger thereon to create a vacuum in one end of the injector after the patient's skin has been pierced to assist in drawing blood from the puncture site by manually moving the lancet guide from a neutral position to a vacuum position.

33 Claims, 3 Drawing Sheets

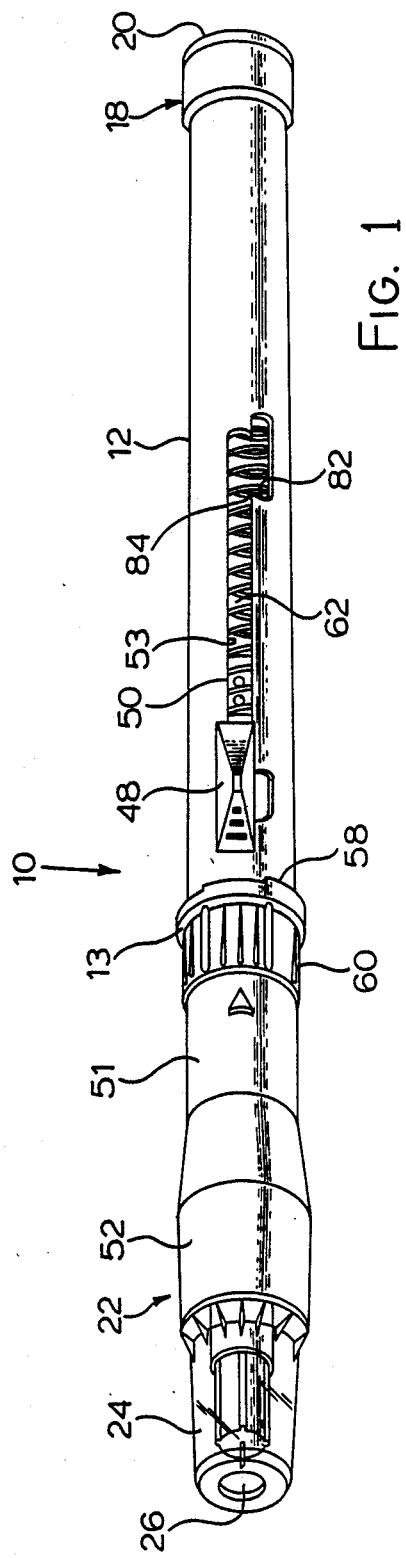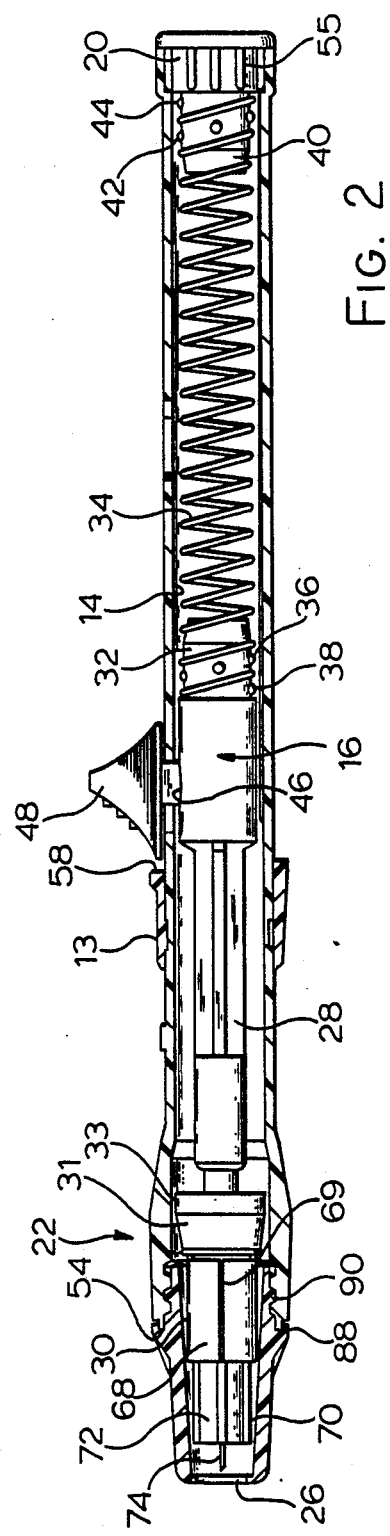

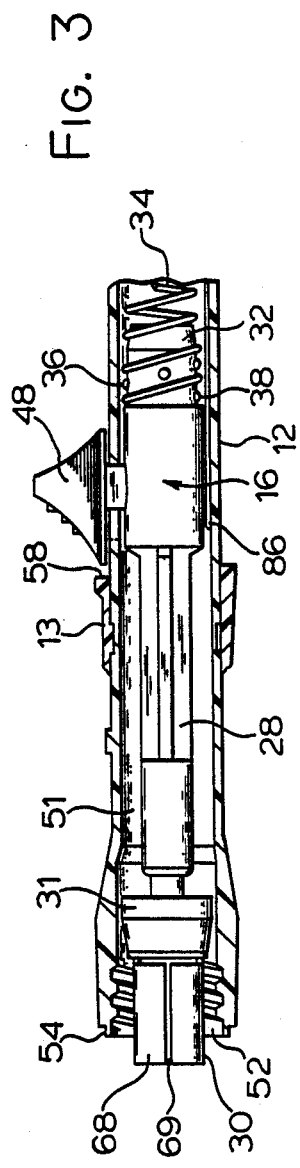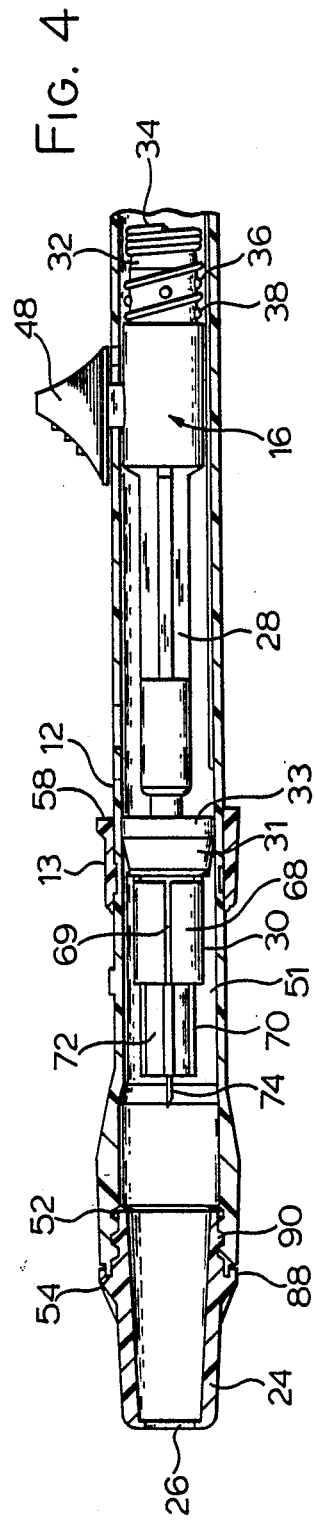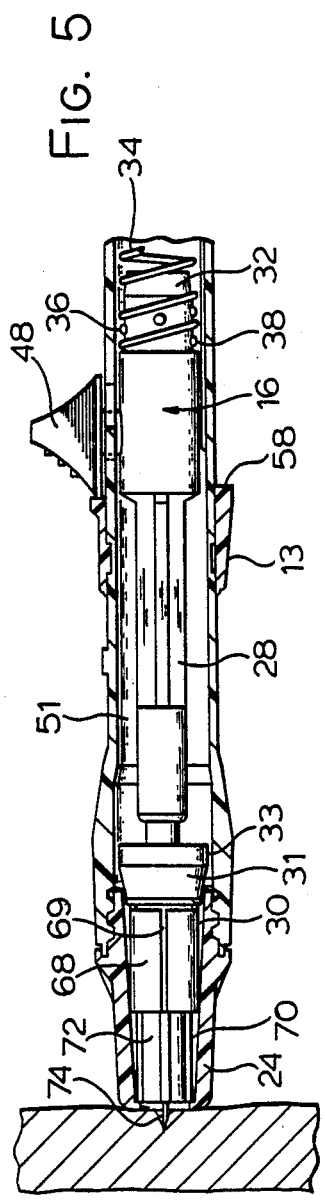

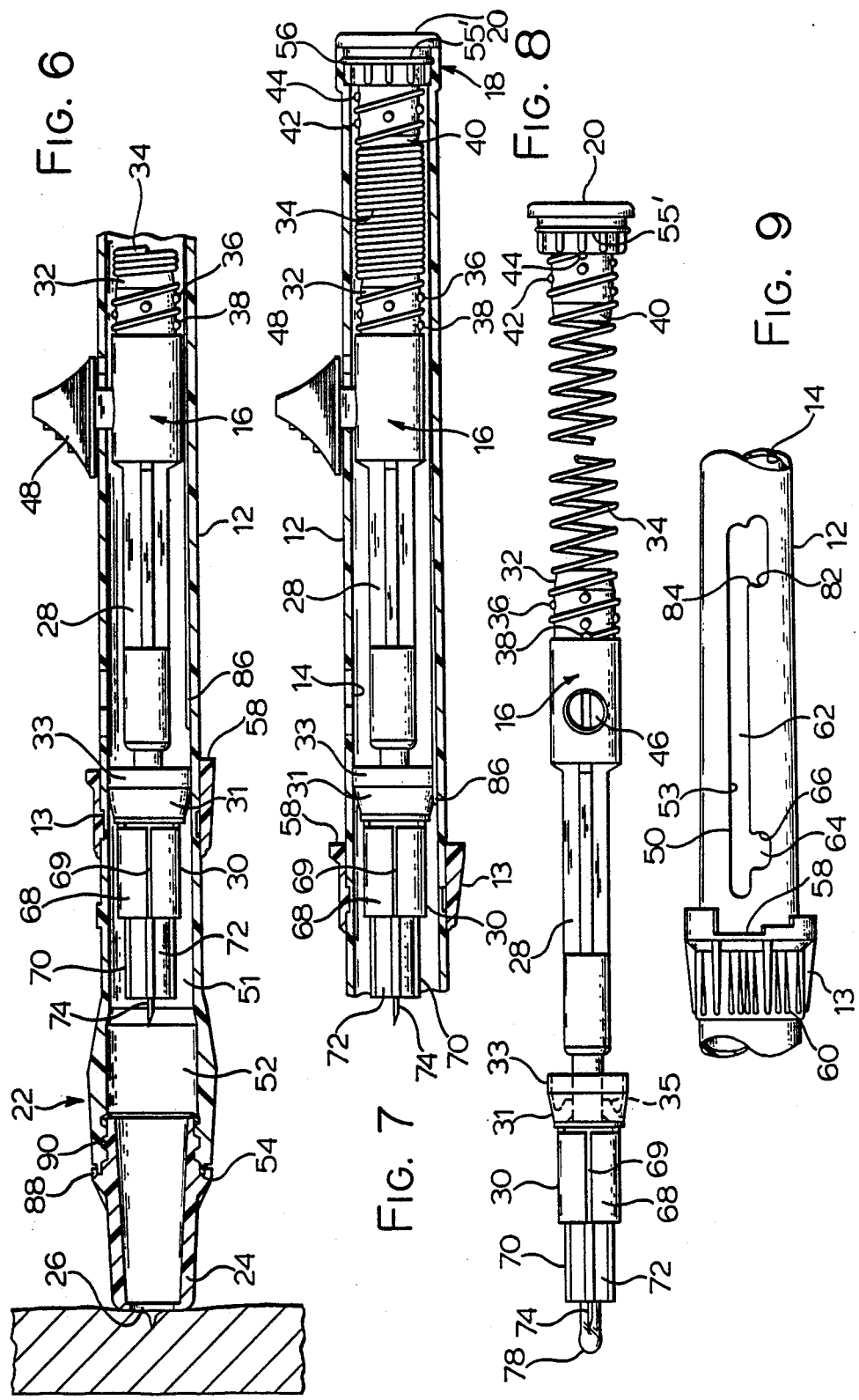

LANCET INJECTOR

TECHNICAL FIELD

This invention relates to lancet injectors, and more particularly to an improved lancet injector adapted for use with single use or disposable lancets for obtaining blood samples for test purposes.

BACKGROUND OF THE INVENTION

Lancets are employed with a variety of devices to make a quick puncture or penetration of the patient's skin in order to obtain a small sample of blood. Various tests may be employed using only small amounts of blood so that the blood flowing from a finger prick is normally sufficient. However, due to the numerous nerve endings in the finger tip area, this procedure may induce a significant amount of pain in the patient even though the skin puncture produces a relatively small cut. Additionally, many patients are required to make numerous finger sticks each day which may result in a coarsening of the finger tip area and a potential loss of tactile discrimination. In order to minimize the potential pain, it is therefore desireable to make the thrust of the lancet through the patient's skin rapidly and at the minimum depth necessary to obtain a sufficient blood sample.

Lancets generally include a body section and a sharpened point extending from one end of the body section. In some instances, the lancet may be physically grasped between the thumb and index finger and made to pierce the skin, for example, the skin of a patient's finger. The lancet is then removed from the puncture and the blood from the puncture site transferred to a blood collection device, such as a capillary tube, micro blood collection tube or diagnostic reagent strip for clinical testing. Numerous problems are associated with such a procedure. For example, the depth of penetration, the force employed in making the puncture, and the angle of insertion and removal vary depending on the person performing the procedure.

More recently, a variety of spring actuated lancet injectors have been designed in an effort to overcome the problems associated with using the lancet alone, however, they have not been entirely satisfactory. For example, some have been relatively complicated in construction and expensive to make. Some constructions require a plurality of springs and a relatively large number of elements for performing such functions as driving, loading and retracting the lancet. Other constructions provide a lancet injector having a fixed, predetermined puncture depth or which are unable to assist in drawing blood from the puncture site. All of the above considerations are particularly important where the puncture is self-made, for example, when a diabetic performs blood glucose testing at home.

SUMMARY OF THE INVENTION

It is therefore an object of the present invention to provide an improved lancet injector which is relatively economical, simple and effective in use, and which substantially overcomes the above-described problems.

It is a further object of the present invention to provide an improved lancet injector which allows the penetration depth of the lancet to be varied according to the preference of the patient.

It is a further object of the present invention to provide an improved lancet injector which is capable of drawing blood from nearly any puncture site by creating a vacuum at the puncture site.

It is yet another object of the invention to provide an improved lancet having a convenient means for releasing the vacuum pressure from the puncture site once a sufficient blood sample has been obtained.

In accordance with one feature of the present invention, a lancet guide and spring are disposed in a housing. An external control member is operatively connected to the lancet guide to move the lancet guide between a loading position, a retracted position, a puncture position, a vacuum position and a vacuum release position. The control member is releasably positioned in an elongate slot on the external surface of the housing and allows a compressed spring to move the lancet guide from the retracted position to a manually adjustable lancet skin penetration position.

In accordance with another feature of the present invention, the lancet injector includes a tapered front end cap attached to the distal end of the housing and an external control member attached to a lancet and flexible plunger disposed inside the housing. Once the puncture is made by the lancet, the external control member may be manually moved from the incision position to a vacuum position while retaining the lancet injector firmly against the puncture site. As the control member is moved to the vacuum position, a vacuum is created in the distal end of the housing and blood is drawn from the puncture site. Once a sufficient amount of blood has been drawn from the puncture, the external control member is manually moved to a vacuum release position to release the vacuum at the puncture site. The lancet injector is then removed from the puncture site and the blood sample is tested.

An advantage of the present invention is that the improved lancet injector is simple and effective to use and relatively inexpensive to manufacture.

A further advantage of the present invention is that the depth of the puncture created by the lancet is adjustable to accommodate the varying needs of the patient.

A further advantage of the present invention is that the improved lancet injector may be used at a variety of puncture sites, including finger areas and peripheral puncture sites.

A further advantage of the present invention is that the improved lancet injector has the ability to draw blood from the puncture site thereby decreasing the liklihood that multiple puncture sites may be necessary to obtain a single blood sample.

These as well as other objects and advantages of the present invention will become more apparent from the following detailed description and the accompanying drawings.

Brief Description of the Drawings

FIG. 1 is a perspective view of the lancet injector in accordance with the preferred embodiment of the present invention;

FIG. 2 is a cross-sectional view of the lancet injector in the neutral position taken along lines 2—2 of FIG. 1.

FIG. 3 is a partial cross-sectional view of the present invention in the loading position;

FIG. 4 is a partial cross-sectional view of the present invention in the retracted position;

FIG. 5 is a partial cross-sectional view of the present invention in the puncture position;

FIG. 6 is a partial cross-sectional view of the present invention in the vacuum position;

FIG. 7 is a partial cross-sectional view of the present invention in the vacuum release position;

FIG. 8 is a perspective view of the interior components of the present invention; and FIG. 9 is a perspective view illustrating the housing and depth selector of the present invention.

Detailed Description of the Preferred Embodiment

Referring now to the drawings, an improved lancet injector shown herein and is referred to generally as lancet injector 10. The lancet injector 10 includes an elongate, generally cylindrical, housing 12 is preferably constructed of a high density polyethylene and having a penetration depth selector 13 thereon. The housing 12 includes an inner chamber 14 and a lancet guide 16 slidably positioned within the inner chamber 14. Housing 12 has a proximal end 18 having an end plus 20 secured thereon and an open distal end 22. The distal end 22 of the housing 12 is attached to a tapered end cap 24 which includes a central opening 26 therein.

The lancet guide 16 includes a generally cylindrical extension section 28 having an opening 46 thereon and a lancet holder 30 and plunger 31 integrally connected to the distal end of the extension section 28. The lancet guide 16 is supported by four spaced release guides 86 which maintain the lancet guide 16 centrally within the housing 12. Additionally, the release guides decrease the frictional resistance to movement of the lancet guide 16 in the housing 12. The plunger 31 is preferably constructed of a conically shaped compressible rubber and includes an outer side wall 33 and an inner support wall 35 to form a generally V-shaped partial cross-section to allow the plunger 31 to selectively engage the walls of the inner chamber 14 as described below. The proximal end of the extension section 28 includes a cylindrically shaped spring connector 32. A spring 34, shown as a coil compression spring, is disposed in the inner chamber 14 between the lancet guide 16 and the plug 20 on the proximal end 18 of the housing 12. The spring connector 32 is provided with a series of external integral bumps 36 disposed in a spiral arrangement for threadedly receiving and holding the distal end of the spring 34. The spring 34 is threaded onto the spring connector 32 until the end of the spring 34 engages an integral stop bump 38. The end plug 20 is shown provided with an inner extension or spring connector 40 having a series of integral, spirally oriented, bumps 42 to threadedly receive and hold the proximal end of the spring 34. The spring 34 is threaded onto connector 40 until the proximal end of the spring 34 engages an integral stop bump 44. If desired, the spring connectors 32 and 40 may be provided with suitably threaded ends or grooves instead of the series of bumps 36 and 42.

The proximal end of the extension section 28, adjacent to the spring connector 32, includes the opening 46 thereon into which a control member 48 is secured. The control member 48 extends through an elongate slot indicated generally as 50, in the sidewall of the housing 12. The control member 48 extends to the exterior of the housing 12 to provide an exterior mounted manually controllable member for positioning the lancet guide 16 in a variety of positions within the housing 12.

In the preferred embodiment, the diameter of the housing 12 gradually increases from the proximal end 18 to the distal end 22 of the housing 12. The distal end 22 of the housing 12 further includes an enlarged diameter access end 52 and a vacuum section 51 positioned proximal to the access end 52. The access end 52 forms an enlarged diameter chamber on the distal end 22 of the housing 12 to allow the lancet holder 30 and plunger 31 to move freely therethrough. The inner surface of the access end 52 is threaded and includes an annular ridge 54 thereon to provide a secure, airtight connection with the outer lip 88 and exterior threads 90 of the tapered end cap 24. In order to create a consistently reproduceable air tight connection, the annular ridge 54 on the access end 52 is tapered inwardly at approximately a 4° angle while the outer lip 88 on the end cap 24 extends outwardly at approximately a 5° angle and the exterior threads 90 extend inwardly at approximately a 4° angle to cause the annular ridge 54 to deflect inwardly as the end cap 24 is threaded onto the distal end 22 of the housing 12. A penetration depth selector 13 is rotatably positioned near the distal end 22 of the housing 12 adjacent to the distal end of the slot 50. The depth selector 13 has a plurality of variable depth contact edges 58 positioned adjacent to the distal end of the slot 50 and visually readable depth markings 60 thereon to allow the patient to adjust the penetration depth of the lancet 70.

In assembling the lancet device 10, the distal end of the spring 34 may be threaded onto the spring connector 32 of the lancet guide 16. This assembly is then inserted into the distal end 22 of the housing 12. Next, the proximal end of the spring 34 is moved to extend beyond the proximal end 18 of the housing 12 to allow the plug 20 to be threaded thereon. The length of the spring 34 is such that the assembly may be manually rotated in the housing 12 by rotating plug 20 until the opening 46 appears in the slot 50. The control member 48 is then inserted through the slot 50 fixed in the opening 46, for example, by adhesively or solvently bonding the control member 48 to the sidewalls of the opening 46.

In the preferred embodiment, the lancet guide 16 and the control member 48 are preferably spring biased in a clockwise direction of rotation, such that the control member 48 is biased towards engagement with the right sidewall 53 of the slot 50. This may be accomplished by providing the plug 20 with a plurality of longitudinal ribbed areas 55 as illustrated in FIG. 2 or with an annular rib 55' which registers with a second of grooved area 56 on the sidewall of the inner chamber 14 at the proximal end 18 of the housing 12 as illustrated in FIGS. 7 and 8. In this way, after the control member 48 is secured in the opening 46, the plug 20 can be rotated clockwise so that the control member 48 contacts the sidewall 53 of the slot 50. The plug 20 is then rotated a slight amount relative to the lancet guide 16, and inserted into the proximal end 18 of the housing 12 to retain the spring 34 in the biased position. The cooperation of the longitudinal ribbed areas 55 and the housing 12 or the annular rib 55' and the grooved area 56 prevents the plug 20 from rotation once it is inserted into the proximal end 18 of the housing 12 while the spring 34 resiliently biases the lancet guide 16 and control member 48 rightwardly or clockwise towards the right sidewall 53 of the slot 50. The plug 20 is then snapped into the housing 12 or, in the alternative, the plug 20 may be adhesively bonded to the housing 12 by applying a suitable adhesive to the plug 20 prior to its insertion into the housing 12.

The lancet holder 30 is attached to the distal end of the lancet guide 16 and is shown as a sleeve or cylindrical barrel having an expansion slot 69 and sidewalls 68 which frictionally engage the outer peripheral surfaces of a lancet 70. The lancet 70 is shown including a body section 72, preferably constructed of a plastic material, and a lancet tip 74, perferably constructed of stainless steel. The body section 72 is preferably molded about the lancet tip 74 so that the sharpened end of the lancet tip 74 extends outwardly beyond the upper end of the body section 72. The lancet 70 is shown including an integrally molded sheath 78 covering the lancet tip 74. The connection between the sheath 78 and the body section 72 is fragile so that by twisting or rotating the sheath 78 relative to the body section 72, and then removing the sheath 78 from the lancet tip 74, the sharpened end of the lancet tip 74 is exposed. The depth of the lancet holder 30 is less than the length of the body section 72 so that the upper portion of the body section 72 extends beyond the lancet holder 30 and may be grasped, for example, between the thumb and finger, for inserting or removing the lancet 70 from the lancet holder 30.

The slot 50 is shaped so as to have a pair of relatively wide passageways near the proximal and distal ends thereof through which the control member 48 may be moved. In FIG. 3, the control member 48 is shown in its loading position wherein the tapered end cap 24 is removed and the lancet holder 30 is extended beyond the distal end 22 of housing 12 to facilitate the insertion or removal of the lancet 70. This position is achieved by moving the control member 48 distally and to the left against the bias force of the spring 34 from the neutral position (illustrated in FIG. 2) through the elongate slot portion 62. The control member 48 is then moved into the enlarged distal slot portion 64 and into the recess 66 which is formed by the distal extending protrusion 80 to releasably hold the control member 48 in the loading position. As the control member 48 moves distally through the slot portion 62, the spring 34 is stretched and rotated counterclockwise to maintain the control member 48 biased in the recess 66 against the protrusion 80.

FIG. 4 illustrates the lancet injector 10 in its retracted position wherein the control member 48 is retracted to place the lancet guide 16, lancet holder 30, lancet 70 and lancet needle 74 wholly within the distal end 22 of the housing 12 and tapered end cap 24. The control member 48 is shown releaseably positioned within recess 82. A proximally extending protrusion 84 is positioned adjacent to the elongate slot 62 to form the recess 82 which securely holds the lancet guide 16 in the retracted position. When the lancet guide 16 is in the retracted position, the spring 34 is in compression and exerts maximal longitudinal spring force on the on the lancet guide 16 in the distal direction and the protrusion 84 holds the control member 48 in the recess 82 against the clockwise biasing force of the spring 34.

When the control member 48 is manually released from the retracted position (FIG. 4), such as by moving the control member 48 rightward over the protrusion 84, the spring 34 causes the lancet guide 16 to move distally through the inner chamber 14 to a puncture position (FIG. 5) wherein the lancet tip 74 extends beyond the central opening 26 in the tapered end cap 24. As the control member 48 moves distally through the inner chamber 14, the sidewalls 33 of the plunger 31 compress to allow the air in the distal end 22 of the lancet injector 10 to escape around the sidewalls 33 of the plunger 31 thereby minimizing the resistance to forward movement of the spring 34 and lancet guide 16 through the housing 12. Near the distal end of the slot 50, the control member 48 contacts a contact edge 58 on the penetration depth selector 13 to prevent further distal movement of the control member 48 and lancet guide 16. Rotation of the penetration depth selector 13 causes the control member 48 to contact different contact edges 58 and thereby controls the distance the lancet tip 74 protrudes through the central opening 26.

In the puncture position, the spring 34 is stretched to cause the lancet guide 16 and lancet 70 to be rapidly retracted to the neutral position (FIG. 2). Therefore, the point of the lancet tip 74 is retracted or withdrawn from the puncture site immediately after the puncture is made. The spring 34 is sized relative to the housing 12 and tapered end cap 24, such that when the lancet guide 16 and control member 48 are in the neutral position (FIG. 2), the spring 34 is at its free length position or neutral force position and applying neither tension nor compression to the lancet guide 16. When the lancet guide 16 is in the neutral position, the lancet 70 extends into the tapered end cap 24 and the lancet holder 30 and plunger 31 are positioned within the larger diameter access end 52 of the housing 12.

In the neutral position, the lancet injector 10 is pressed tightly against the skin to maintain the contacting relationship between the end cap 24 and the skin and the control member 48 is moved proximally to the vacuum position as illustrated in FIG. 6. As the control member 48 is moved proximally beyond the access end 52 of the housing 12, the sidewalls 33 of the plunger 31 expand and contact the inner sidewalls of the housing 12 in the vacuum section 51 to create a vacuum inside the distal end 22 of the housing 12. In order to apply a constant vacuum pressure, the control member 48 may be returned to the recess 82 wherein the control member 48 is held in position by the protrusion 84. When a sufficient amount of blood has been drawn from the puncture site, the control member 48 is moved proximally to a vacuum release position as illustrated in FIG. 7. As the control member 48 is moved to the vacuum release position, the sidewalls 33 of the plunger 31 are compressed by a plurality of vacuum release guides 86 located along the inner sidewalls of the housing 12. This contact between the sidewalls 33 of the plunger 31 and the release guides 86, releases the vacuum seal between the sidewalls 33 and the housing 12 to allow air to flow through the slot 50 into the distal end 22 of the housing 12 and the tapered end cap 24. By allowing air to flow into the distal end 22 of the housing 12 from the slot 50, to release the vacuum, the blood sample does not splatter against the sidewalls of the end cap 24 on the access end 52 of the housing 12. Once the vacuum pressure is released, the lancet injector 10 is removed from the puncture site, and the lancet guide 16 is preferably returned to the neutral position.

In operation, a new lancet, such as lancet 70, is initially inserted into the lancet holder 30 when the control member 48 is positioned in the lancet loading position as illustrated in FIG. 3. The sheath 78 is then removed from the lancet tip 74 and the control member 48 is manually moved out of the recess 66 so that the spring 34 automatically withdraws the lancet 70 into the distal end 22 of the housing 12 as indicated in FIG. 2. The end cap 24 is then threaded onto the distal end 22 of the housing 12 so that the outer lip 88 and the exterior threads 90 of the tapered end 24 contact the annular ridge 54 of the housing 12 to form an airtight seal between the end cap 24 and the access end 52 of the the housing 12.

Next, a lubricant may be applied to the distal end of the end cap 24 surrounding the central opening 26 to ensure a good seal against coarse skin textures and/or hair. The control member 48 is then moved proximally in the slot 50 until the control member 48 reaches the retracted position in recess 82. Next, the penetration depth selector 13 is rotated to select the preferred penetration depth of the lancet 70 for the selected puncture site. Once the control member 48 is placed in the retracted position (FIG. 4), the housing 12 is grasped by the patient's hand and the end cap 24 is pressed against the finger or any other site suitable for obtaining a blood sample.

The control member 48 is then moved to the right and out of the retracted position so that the force of the spring 34 and the inertia of the lancet 70 and lancet guide 16 effect a piercing of the skin by the lancet tip 74 as the control member 48 contacts a contact edge 58 on the penetration depth selector 13 (FIG. 5). The spring 34 then automatically retracts the lancet tip 74 from the puncture site to the neutral position as indicated in FIG. 2. Once the lancet guide 16 is in the neutral position, the lancet injector 10 is pressed firmly against the skin and the control member 48 is moved proximally to the vacuum position as illustrated in FIG. 6. As the control member 48 is moved to the vacuum position, the plunger 31 passes through the access end 52 of the housing 12 and into the vacuum section 51 of the housing 12. As the plunger 31 enters the vacuum section 51, the sidewalls 33 of the plunger 31 contact the inner walls of the vacuum section 51 to create an airtight seal between the plunger 31 and the housing 12. As the lancet guide 16 is moved further, the air in the access end 52 and the tapered end cap 24 is forced to expand into this enlarged chamber and a vacuum is created to draw blood from the puncture site. If the blood flow from the selected puncture site is slow, the control member 48 may be moved into the recess 82 to apply a constant vacuum to the puncture site until a sufficient amount of blood has been drawn from the puncture site.

The control member 48 is then moved proximally from the vacuum position to the vacuum release position (FIG. 7) to cause the sidewalls 33 of the plunger 31 to contact the release guides 86 on the inner wall of the housing 12 and thereby release the vacuum created in the distal end 22 of the housing 12. Once the vacuum is released, the lancet injector 10 is removed from the patient's skin and the control member 48 is moved to the neutral position. The blood from the puncture site is then transferred to a blood collection device such as a a capillary tube, micro blood collection tube or a diagnostic reagent strip.

In addition to providing a lancet injector 10 which applies vacuum to an adjustable depth puncture site, the preferred embodiment of the present invention also allows the distal force of the spring 34 and lancet guide 16 to be varied by the user. If the user desires a rapid, forceful puncture, the lancet injector 10 may be pressed firmly against the skin prior to moving the control member 48 to the retracted position. This procedure create a vacuum in the distal end 22 of the lancet injector 10 to assist in the forward movement of the spring 34 and creates a vacuum in the distal end 22 of the lancet injector 10 to draw the lancet guide 16 forward when the control member 48 is released from the retracted position. If a slower, less forceful puncture is desired, the lancet injector 10 may be placed in contact with the skin after the control member 48 is placed in the retracted position. This procedure resists the forward movement of the spring 34 and creates a resistance to the forward movement of the lancet guide 16 by causing the air in the distal end 22 of the lancet injector 10 to flow aroud the compressed plunger 33 as the lancet guide 16 moves distally to the puncture position. Various intermediate reproducable puncturing speeds and forces may be obtained with the present invention by holding the control guide 48 in any position between the neutral and retracted positions prior to placing the lancet injector 10 in contact with the user's skin.

The cleaning and preparation of the lancet injector 10 is designed to be simple and may be accomplished in a relatively short time. Initially, the tapered end cap 24 is removed from the distal end 22 of the housing 12 and cleaned. When the patient desires to obtain a new blood sample, the end cap 24 is removed to allow the new lancet 70 to be inserted into the lancet holder 30. The sheath 78 is then removed from the lancet 70 and the end cap 24 is threaded onto the distal end 22 of the housing 12. The lancet injector 10 is now ready to obtain another blood sample.

As various changes may be made in the construction of the invention without departing from the scope thereof, it is intended that all matter contained in the description of the preferred embodiment and shown in the accompanying drawings shall be interpreted as merely illustrative of one form of the invention and not in any way limiting the true scope of the invention as defined by the attached claims.

What is claimed is:

1. A lancet injector comprising
a generally elongate housing having distal and proximal ends and a generally longitudinally extending slot in the sidewall thereof said slot in communication with an inner chamber in said housing wherein said inner chamber extends from the distal end of said housing and into the proximal end of said housing,
a lancet guide having distal and proximal ends wherein said distal end includes a means for retaining a lancet thereon,
a spring means in said inner chamber wherein said spring means actuates movement of said lancet guide in said inner chamber,
a control member connected to said lancet guide and extending through said slot to the exterior of said housing, wherein said control member is moveable distally from a retracted position to an puncture position in said slot wherein said lancet guide moves against the force of said spring means to the retracted position and substantially with the force of the spring means to the puncture position, and
a penetration depth selector on said housing wherein the distance between the retracted position of said control member and the puncture position of said control member may be adjusted to vary the depth of the puncture created by the lancet in the puncture position.

2. The lancet injector of claim 1, wherein the penetration depth selector includes a plurality of contact edges wherein the puncture position of said control member is determined by the relative height of the contact edge selected to contact said control member.

3. The lancet injector of claim 2, wherein the penetration depth selector rotates about the exterior of said housing to align one of said contact edges with said control member.

4. The lancet injector of claim 1, wherein said lancet guide includes a plunger thereon positioned proximally to said lancet retaining means whereby a vacuum is created in the distal end of said housing when said control member is moved proximally from a neutral position proximal of the puncture position to a vacuum position.

5. The lancet injector of claim 4, wherein the distal end of the housing includes an enlarged diameter area adjacent to the plunger when said plunger is in the puncture position.

6. The lancet injector of claim 5, wherein proximal movement of the lancet guide from the neutral position causes movement of the plunger from the enlarged diameter area to a vacuum section of said housing wherein the plunger frictionally contacts the interior of said housing.

7. The lancet injector of claim 4, wherein the distal end of the housing includes a removable end cap thereon and said end cap includes an opening therein to allow the lancet to extend therethrough.

8. The lancet injector of claim 1, wherein the control member is movement proximally from a neutral position proximal of the puncture position to a vacuum position wherein a plunger on said lancet guide is moveable to a contacting relation with the inner chamber of said housing to create a vacuum in the distal end of said housing as said control member is moved proximally from the neutral position and wherein said plunger releases the inner surface of said housing when the control member is moved distally from the retracted position to the puncture position.

9. The lancet injector of claim 8, wherein the plunger is a flexible member having a generally conical shape and is positioned proximal to said lancet retaining means on said lancet guide.

10. The lancet injector of claim 8, wherein the control member is movable from the vacuum position to a vacuum release position wherein the plunger release the vacuum in the distal end of said housing is released.

11. The lancet injector of claim 10, wherein the plunger contacts a vacuum release guide in the inner chamber of said housing when said control member is moved proximally from the vacuum position to the vacuum release position.

12. The lancet injector of claim 1, wherein the inner chamber of said housing includes a plurality of release guides therein to support said lancet guide therein and decrease frictional resistance to the movement thereof.

13. A lancet injector for obtaining blood from a puncture site on a patient comprising
a generally elongate housing having an inner chamber, a closed proximal end and an open distal end,
a lancet guide movable in said inner chamber and including proximal and distal ends wherein said distal end includes a lancet retaining means and a plunger aligned proximal to said lancet retaining means on said lancet guide, and
said lancet guide being moveable between a loading position wherein a lancet is inserted into the lancet retaining means, a retracted position wherein the lancet guide is positioned proximal to the distal end of the housing, a puncture position distal to said retracted position wherein the lancet creates a puncture on the patient's skin, a vacuum position proximal to the puncture position wherein the plunger contacts the inner chamber of the housing to create a vacuum in the distal end of said housing as the lancet guide moves to the vacuum position and a vacuum release position wherein movement of the lancet guide from the vacuum position releases the contact between the plunger and the inner chamber of the housing.

14. The lancet injector of claim 13, wherein the distal end of said housing includes an enlarged diameter area wherein said plunger contacts the inner chamber of said housing proximal to said enlarged diameter area and wherein a vacuum is created in the enlarged diameter area when said lancet guide is moved from a neutral position proximal of the puncture position to the vacuum position.

15. The lancet injector of claim 14, wherein the distal end of said housing is removably attached to an end cap having distal and proxmal ends wherein the distal end of said end cap is placed in a contacting relation with the skin of a patient to form a seal with the skin of the patient when said lancet guide is moved from the neutral position to the vacuum position.

16. The lancet injector of claim 15, wherein said end cap includes an opening in the distal end thereof and wherein a lancet tip on the lancet extends beyond the distal end of said end cap when said lancet guide is moved from the retracted position to the puncture position.

17. The lancet injector of claim 15, wherein the proximal end of the end cap is threaded onto the distal end of the housing to create a substantially air tight seal therebetween when said lancet guide is moved from the neutral position to the vacuum position.

18. The lancet injector of claim 13, wherein the housing includes a depth adjusting means thereon to adjust the distance between the retracted position and puncture position of the lancet guide.

19. The lancet injector of claim 18, wherein rotation of said depth adjusting means changes the depth of the puncture created by the lancet when the lancet guide is moved from the retracted position to the puncture position.

20. A lancet injector comprising
an outer elongate housing having an open distal end and a closed proximal end and a generally longitudinally directed slot therein extending from an inner chamber in said housing to the exterior surface of said housing and further including an enlarged diameter area on said distal end,
a lancet guide having distal and proximal ends moveable positioned in said inner chamber of said housing and wherein said distal end includes a lancet retaining means thereon,
a lancet having a lancet tip thereon and body section wherein said body section is removably retained in the lancet retaining means,
a flexible plunger on said distal end of said lancet guide positioned adjacent to said lancet retaining means on said lancet guide,
a spring means in said inner chamber of said housing wherein the spring means extends from the proximal end of said housing to the proximal end of said lancet guide to actuate movement of said lancet guide through said inner chamber, and
a control member attached to said lancet guide wherein said control member extends throught the slot to the exterior of the housing and is moveable from a puncture position wherein the skin of a patient is pierced by the lancet tip on said lancet to a vacuum position wherein the plunger contacts the inner chamber of said housing proximal to said enlarged diameter area to create a vacuum in the distal end of said housing.

21. The lancet injector of claim 20, wherein the distal end of said housing further includes a removable end cap thereon wherein the end cap forms a substantially air tight seal with the skin of the patient when the air cap is placed in contact with the patient's skin and wherein a vacuum is created therein when the control member is moved from a neutral position near the puncture position to the vacuum position.

22. The lancet injector of claim 21, wherein the end cap includes an outwardly tapered lip and an inwardly directed extension for releasably engaging a tapered annular ridge on the distal end of said housing to form a substantially air tight seal therebetween.

23. The lancet injector of claim 20, wherein the control member is further moveable to a loading position wherein the lancet retaining means projects the lancet beyond the distal end of said housing for the removable insertion of a lancet in the lancet retaining means.

24. The lancet injector of claim 23, wherein the slot includes a retaining lip thereon for releasably retaining the control member in the loading position against the force of the spring means.

25. The lancet injector of claim 20, wherein the control member is moveable distally from the retracted position to the puncture position by the force of the spring means and wherein the control member is moved proximally from a neutral position proximal of the puncture position to the vacuum position against the force of the spring means and wherein the retracted position and vacuum position of the control member are substantially identical.

26. The lancet injector of claim 25, wherein the plunger is generally conically shaped and includes an outer sidewall and an inner support wall wherein the outer sidewall contacts the inner chamber in the vacuum position and is compressed as the control member moves distally from the retracted position to the puncture position.

27. The lancet injector of claim 25, wherein the control member is moveable proximally from the vacuum position to a vacuum release position against the force of the spring means.

28. The lancet injection of claim 20, wherein the slot includes a retaining lip thereon for releasably retaining the control member in the retracted position against the force of the spring means.

29. The lancet injector of claim 20, wherein the housing further includes a penetration depth selector arranged in a contacting relation with the control member and wherein rotation of the penetration depth selector adjusts the depth of the puncture created by the lancet on the skin of the patient.

30. A method of obtaining a blood sample from a patient comprising the steps of
moving a lancet guide substantially enclosed within an inner chamber of a elongate housing having distal and proximal ends to a retracted position wherein the lancet guide having a lancet retaining means and lancet thereon are surrounded by the distal end of said housing,
releasing said lancet guide from said retracted position so that a spring means compressed in said inner chamber moves said lancet guide distally to a puncture position wherein a lancet tip on said lancet pierces the skin of a patient to create a puncture site on the patient,
moving said lancet guide proximally from the puncture position to a vacuum position wherein a plunger on said lancet guide contacts the sidewalls of the inner chamber to create a vacuum in the distal end of said housing as the lancet guide is moved proximally to the vacuum position, and
releasing the vacuum in the distal end of said housing by moving the lancet guide from the vacuum position to a vacuum relase position wherein the plunger is released from the contacting relation with the inner chamber of said housing.

31. The method of claim 30 wherein the depth of the puncture site on the patient is adjustable by rotating a penetration depth selector on said housing before the lancet guide is released from the retracted position.

32. The method of claim 30 wherein the distal movement of the lancet guide may be accelerated by placing the distal end of the housing in contact with the skin of the patient prior to moving the lancet guide to the retracted position.

33. The method of claim 30 wherein the distal movement of the lancet guide may be decreased by placing the distal end of the housing in contact with the skin of the patient after the lancet guide is moved to the retracted position.

* * * * *